(12) United States Patent
Punjani et al.

(10) Patent No.: US 12,362,037 B2
(45) Date of Patent: Jul. 15, 2025

(54) METHODS AND SYSTEMS FOR RECONSTRUCTION OF THREE-DIMENSIONAL STRUCTURE AND THREE-DIMENSIONAL MOTION OF A PROTEIN MOLECULE

(71) Applicant: STRUCTURA BIOTECHNOLOGY INC., Toronto (CA)

(72) Inventors: Ali Punjani, Toronto (CA); David Fleet, Toronto (CA)

(73) Assignee: STRUCTURA BIOTECHNOLOGY INC., Toronto (CA)

( * ) Notice: Subject to any disclaimer, the term of this patent is extended or adjusted under 35 U.S.C. 154(b) by 0 days.

(21) Appl. No.: 18/042,552

(22) PCT Filed: Apr. 21, 2022

(86) PCT No.: PCT/CA2022/050614
§ 371 (c)(1),
(2) Date: Feb. 22, 2023

(87) PCT Pub. No.: WO2022/221956
PCT Pub. Date: Oct. 27, 2022

(65) Prior Publication Data
US 2023/0335216 A1    Oct. 19, 2023

Related U.S. Application Data

(60) Provisional application No. 63/201,260, filed on Apr. 21, 2021.

(51) Int. Cl.
*G16B 15/20* (2019.01)
*G16B 40/20* (2019.01)
(Continued)

(52) U.S. Cl.
CPC ............ *G16B 15/20* (2019.02); *G16B 40/20* (2019.02); *G16C 20/30* (2019.02); *G16C 20/70* (2019.02)

(58) Field of Classification Search
CPC .............................. G16C 20/30; G16C 20/70
See application file for complete search history.

(56) References Cited

U.S. PATENT DOCUMENTS

2017/0103161 A1*  4/2017  Brubaker ............... G16B 15/00
2020/0066371 A1   2/2020  Brubaker et al.

FOREIGN PATENT DOCUMENTS

CA       3078256 A1    4/2019
CA       3140807 A1    12/2020
(Continued)

OTHER PUBLICATIONS

Zhong et al., CryoDRGN: reconstruction of heterogenous cry-EM structures using neural networks, Feb. 2021, Nature Methods, 18, p. 176-185 (Year: 2021).*

(Continued)

*Primary Examiner* — Kaitlyn L Minchella
(74) *Attorney, Agent, or Firm* — Bhole IP Law; Marc Lampert

(57) ABSTRACT

Provided are systems and methods for determining 3D structure and 3D motion of a protein molecule from 2D or 3D particle observation images. The method includes: initializing pose parameters and unknown model parameters;
(Continued)

performing image formation which includes: generating one or more 3D deformation fields by inputting a latent coordinate vector into the one or more flow generators; performing a convection and projection operation; and performing CTF corruption; fitting the unknown model parameters to the experimental images by gradient-based optimization of an objective function; latent variable search for a given experimental image which includes: performing the image formation one or more times to generate simulated images; and selecting one or more latent coordinate vectors based on similarity; and updating the at least one of the unknown model parameters which includes: generating simulated images; and evaluating the objective function; computing the gradient of the objective function.

21 Claims, 10 Drawing Sheets

(51) Int. Cl.
*G16C 20/30* (2019.01)
*G16C 20/70* (2019.01)

(56) References Cited

FOREIGN PATENT DOCUMENTS

| WO | 2019018040 | A9 | 3/2019 |
|----|------------|----|--------|
| WO | 2020058174 | A1 | 3/2020 |

OTHER PUBLICATIONS

Barnett, A. et al., Rapid Solution of the Cryo-EM Reconstruction Problem by Frequency Marching, SIAM Journal on Imaging Sciences, vol. 10, issue 3, pp. 1170-1195, Aug. 1, 2017 (Jan. 8, 2017).
International Search Report of the Canadian Intellectual Property Office acting as the International Searching Authority for International application No. PCT /CA2022/050614; dated Jul. 11, 2022.
L. Yumkis, D., Challenges and opportunities in cryo-EM single-particle analysis, The Journal of biological chemistry, vol. 294, issue 13, pp. 5181-5197, Feb. 25, 2019 (Feb. 25, 2019).
Punjani, A. et al., 3D Flexible Refinement: Structure and Motion of Flexible Proteins 1-23 from Cryo-EM, bioRxiv, Apr. 22, 2021 (Apr. 22, 2021).
Punjani, A. et al., 3D variability analysis: Resolving continuous flexibility and discrete heterogeneity from single particle cryo-EM, Journal of Structural Biology, vol. 213, issue 2, Feb. 11, 2021 (Feb. 11, 2021).
Singer, A. et al., Computational Methods for Single-Particle Electron Cryomicroscopy, Annual Review of Biomedical Data Science, vol. 3, issue 1, pp. 163-190, Jul. 20, 2020 (Jul. 20, 2020).
Written Opinion of the Canadian Intellectual Property Office acting as the International Searching Authority for International application No. PCT /CA2022/050614; dated Jul. 11, 2022.
Phong, E. D. et al., CryoDRGN: Reconstruction of heterogeneous cryo-EM structures using neural networks, Nature Methods, vol. 18, issue 2, pp. 176-185, Feb. 4, 2021 (Feb. 4, 2021).

* cited by examiner

METHODS AND SYSTEMS FOR RECONSTRUCTION OF THREE-DIMENSIONAL STRUCTURE AND THREE-DIMENSIONAL MOTION OF A PROTEIN MOLECULE

TECHNICAL FIELD

The following relates generally to electron Cryo-microscopy; and more specifically, to systems and methods for reconstruction of three-dimensional structure and three-dimensional motion of a protein molecule.

BACKGROUND

Proteins form the molecular machinery of the cell. They are inherently dynamic, often exhibiting a continuous landscape of energetically favorable conformations, with motion tightly coupled to function. Methods that uncover protein motion and the conformational landscape have the potential to illuminate fundamental questions in structural biology, and to enhance our ability to design therapeutic molecules that elicit specific functional changes in a target protein. Revealing protein dynamics is a frontier of structural biology, and in the absence of experimental techniques, molecular dynamics simulation and other approximate predictions have been widely adopted.

Single particle cryo-EM collects thousands of static two-dimensional (2D) protein particle images that, in aggregate, span the target protein's three-dimensional (3D) conformational space. Cryo-EM therefore is potentially able to experimentally uncover both the atomic-resolution structure and motion of biologically functional moving parts. Nevertheless, methods for resolving continuous motion and structure from static 2D images have remained elusive.

SUMMARY

In an aspect, there is provided a method for determining the three-dimensional (3D) structure and 3D motion of a molecule from two-dimensional (2D) or 3D experimental images, the 3D structure in the form of one or more canonical 3D maps, and the 3D motion in the form of parameters of one or more flow generators, the method comprising: receiving the experimental images; receiving contrast transfer function (CTF) parameters for each experimental image; initializing pose parameters for each experimental image; initializing unknown model parameters of image formation, the unknown model parameters comprising: one or more canonical 3D maps; and the parameters of the one or more flow generators, each flow generator comprising a parameterized generator function taking as input a latent coordinate vector and outputting a 3D deformation field; wherein the image formation taking as input at least a latent coordinate vector and outputting a simulated image, the image formation comprising: generating one or more 3D deformation fields by inputting the latent coordinate vector into the one or more flow generators; performing a convection and projection operation by convecting one or more of the canonical 3D maps by the one or more 3D deformation fields, and projecting using the pose parameters for the given experimental image; and performing CTF corruption of the projected result using the CTF parameters of the given experimental image to generate the simulated image; fitting the unknown model parameters to the experimental images by performing one or more iterations of gradient-based optimization of an objective function, the objective function taking as input at least simulated images and experimental images, wherein in at least one of the iterations, performing latent variable search for at least one experimental image, latent variable search for a given experimental image comprising: performing the image formation one or more times to generate simulated images from one or more latent coordinate vectors; and selecting one or more latent coordinate vectors based on the similarity between simulated images and the experimental image; and wherein in at least one of the iterations, updating at least one of the unknown model parameters using at least one of the experimental images, updating the at least one of the unknown model parameters comprising: generating simulated images by performing the image formation using the one or more selected latent coordinate vectors associated with the experimental images; evaluating the objective function using at least the simulated images and the experimental images; computing the gradient of the objective function with respect to the at least one unknown model parameter to be updated; and updating the unknown model parameter using the gradient; and outputting the one or more canonical 3D maps, the parameters of the one or more flow generators, or both.

In a particular case, the pose parameters for each experimental image are initialized by receiving them as input.

In another case, the experimental images and the simulated images are 2D.

In yet another case, the canonical 3D map is represented as a 3D voxel array of real-space density values.

In yet another case, the convection and projection operation comprises interpolating the canonical 3D map to form the convected and projected image, the interpolation operation defined by the deformation field and the pose parameters.

In yet another case, the flow generator is a feed-forward neural network.

In yet another case, a 3D deformation field is represented as deformed positions of vertices of a mesh of volumetric elements, the deformation vector field values defined by interpolation within the volume of each mesh element.

In yet another case, the objective function comprises at least the negative log-likelihood of a simulated image given an experimental image using a noise model.

In yet another case, the noise model is a Gaussian noise model

In yet another case, the latent variable search comprises coordinate descent search over the latent coordinate vector space.

In yet another case, the latent variable search comprises gradient descent search over the latent coordinate vector space.

In yet another case, the latent variable search comprises selecting latent coordinate vectors that are equal to the latent coordinate vectors determined to optimize the similarity plus a component of random noise.

In yet another case, each iteration of the gradient-based optimization comprises selecting a random subset of the experimental images.

In yet another case, updating at least one of the unknown model parameters using the gradient is performed using the Adam update rule.

In yet another case, updating at least one of the unknown model parameters using the gradient is performed using the Stochastic Gradient Descent update rule.

In yet another case, updating at least one of the unknown model parameters using the gradient is performed using the Stochastic Gradient Descent with momentum update rule.

In yet another case, updating at least one of the unknown model parameters using the gradient is performed using the L-BFGS update rule.

In yet another case, updating the canonical 3D map using the gradient is performed using the L-BFGS update rule.

In yet another case, the objective function comprises regularizing terms.

In yet another case, regularizing terms comprise terms that penalize non-rigid deformation in a 3D deformation field.

In yet another case, a 3D deformation field is represented as deformed positions of vertices of a mesh of volumetric elements, the deformation vector field values defined by interpolation within the volume of each mesh element, and regularizing terms comprise terms that penalize non-rigid deformation within each mesh element.

In yet another case, the optimization of the unknown model parameters is performed using spatial frequency marching In yet another case, the optimization of the unknown model parameters is first performed using a lower spatial frequency limit and subsequently performed using a higher spatial frequency limit.

These and other aspects are contemplated and described herein. It will be appreciated that the foregoing summary sets out representative aspects of systems and methods to assist skilled readers in understanding the following detailed description.

DESCRIPTION OF THE DRAWINGS

The features of the invention will become more apparent in the following detailed description in which reference is made to the appended drawings wherein.

DETAILED DESCRIPTION

Figure 1:
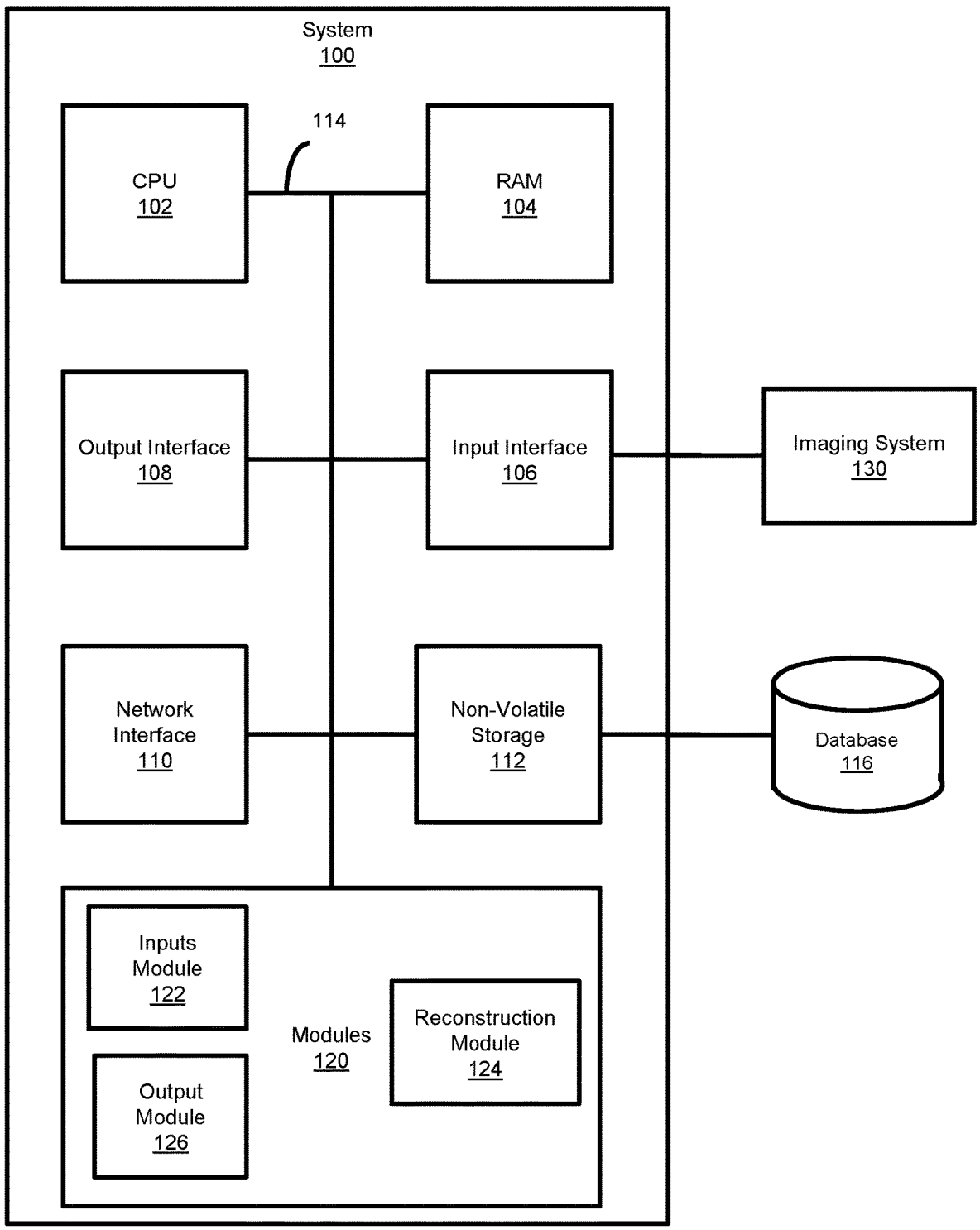
FIG. 1 shows a system for reconstruction of three-dimensional structure and three-dimensional motion of a protein molecule, according to an embodiment.

For simplicity and clarity of illustration, where considered appropriate, reference numerals may be repeated among the Figures to indicate corresponding or analogous elements. In addition, numerous specific details are set forth in order to provide a thorough understanding of the embodiments described herein. However, it will be understood by those of ordinary skill in the art that the embodiments described herein may be practiced without these specific details. In other instances, well-known methods, procedures and components have not been described in detail so as not to obscure the embodiments described herein. Also, the description is not to be considered as limiting the scope of the embodiments described herein.

Various terms used throughout the present description may be read and understood as follows, unless the context indicates otherwise: "or" as used throughout is inclusive, as though written "and/or"; singular articles and pronouns as used throughout include their plural forms, and vice versa; similarly, gendered pronouns include their counterpart pronouns so that pronouns should not be understood as limiting anything described herein to use, implementation, performance, etc. by a single gender; "exemplary" should be understood as "illustrative" or "exemplifying" and not necessarily as "preferred" over other embodiments. Further definitions for terms may be set out herein; these may apply to prior and subsequent instances of those terms, as will be understood from a reading of the present description.

Any module, unit, component, server, computer, terminal, engine or device exemplified herein that executes instructions may include or otherwise have access to computer readable media such as storage media, computer storage media, or data storage devices (removable and/or non-removable) such as, for example, magnetic disks, optical disks, or tape. Computer storage media may include volatile and non-volatile, removable and non-removable media implemented in any method or technology for storage of information, such as computer readable instructions, data structures, program modules, or other data. Examples of computer storage media include RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by an application, module, or both. Any such computer storage media may be part of the device or accessible or connectable thereto. Further, unless the context clearly indicates otherwise, any processor or controller set out herein may be implemented as a singular processor or as a plurality of processors. The plurality of processors may be arrayed or distributed, and any processing function referred to herein may be carried out by one or by a plurality of processors, even though a single processor may be exemplified. Any method, application or module herein described may be implemented using computer readable/executable instructions that may be stored or otherwise held by such computer readable media and executed by the one or more processors.

Established high-resolution cryo-EM refinement methods often assume rigidity of the target molecule, and result in blurred, low resolution density for flexible regions. Methods with spatially adaptive regularization mitigate the adverse effects of local motion on rigid refinement, but do not estimate the motion per se. Local refinement and multi-body methods use masks to focus on a sub-region of a protein, but only provide improved resolution on rigid parts of relatively large molecular weight. Subspace methods approximate a particle's space of conformation as a linear combination of basis density maps, but without an underlying concept of motion.

The development of a method that, in the presence of continuous flexibility, can uncover protein motion and thereby improve the resolution of fine structural details is a substantial technical problem. Effective solutions face several key challenges. First, there are a large number of unknowns that must be jointly estimated from the data, including the 3D structure of the density map, a representation of the space of conformational changes, and the position of each particle image on that conformational landscape. Second, the protein motion and the conformational landscape are generally non-linear. Third, in order to resolve 3D map details beyond what conventional (static) reconstructions can provide, structural information must be aggregated from many different conformations. Finally, despite the high levels of noise, and computational difficulty of the underlying optimization problem, the unknowns must be estimated with enough precision to enable recovery of high-resolution details.

The present embodiments advantageously provide an approach for 3D Flexible Refinement (referred to informally as '3DFlex'), a deep neural network model of continuously flexible protein molecules. 3DFlex is a motion-based heterogeneity model that directly exploits the notion that conformational variability of a protein is a result of physical processes which tend conserve mass and preserve the local geometry of the underlying molecular structure. This is in contrast to density-based techniques that model conformational variation as a manifold of 3D density maps without a physically plausible motion model that explicitly captures the transport of density from one location to another. Some approaches have also sought to model motion in limited forms. The formulation of 3DFlex is based on a generative architecture that captures conformational variability in terms of a single high-resolution canonical 3D density map of the molecule, and a parameterized latent space of deformation fields encoding non-rigid motion. The deformation fields "bend" the canonical density via convection, yielding all conformations captured by the model. In 3DFlex canonical density, the deformation field generator, and the latent coordinates of each particle image are jointly learned from the image data using a specialized training algorithm, without any prior knowledge about the flexibility of the molecule.

Results obtained with experimental cryo-EM data show that 3DFlex effectively addresses the challenges of flexible refinement. We show that the model can jointly learn the structure of the flexible molecule, the underlying non-linear, non-rigid motion that unites its conformational landscape, and the positions of each single particle image on that landscape. Given a dataset of tri-snRNP spliceosome particles, 3DFlex learns non-rigid motions that range from a α-helices and β-sheets moving fractions of an Angstrom to the large motions of sub-units bending across a span of 20+Å. In doing so, it aggregates structural information from all conformations into a single, optimized density map where high-resolution features of flexible domains are well-resolved. In fact, 3DFlex can model continuous motion with enough precision to improve the resolution of small flexible parts that are otherwise poorly resolved in both conventional and local focused refinements; which the experiments demonstrate on a dataset of TRPV1 ion-channel particles; where 3DFlex improves FSC resolution and map quality of peripheral α-helices in the flexible soluble domains.

The present embodiments provide an approach to determine both the structure and motion of flexible particles, and effectively use the motion to enhance map detail. This determination allows for the study of biological mechanisms and function involving motion, at the frontier of both cryo-EM and structural biology.

The present embodiments can have several possible variations, as understood by a person skilled in the art and should not be limited to variations specifically described herein. The present embodiments provide a substantial improvement in the field of structural biology of protein molecules, which generally requires simultaneous consideration of hundreds of thousands of non-trivial numerical representations of 3D protein structures with high precision.

The present embodiments provide a generative neural network method that determines the structure and motion of flexible protein molecules from input cryo-EM images of individual molecules, referred to herein as experimental image or a particle image. The experimental images can be two dimensional (2D) or three dimensional (3D) images resulting from, in some instances, single-particle cryo-electron microscopy, and in some other instances cryo-electron tomography; though in general they can result from any type of particle imaging approach. Generally, multiple conformations of a dynamic protein are related to each other through deformation of a single 3D structure. Specifically, the maps for flexible molecule are represented in terms of i) a canonical 3D map, ii) latent coordinate vectors that specify positions over the protein's conformational landscape, and iii) a flow generator that converts a latent coordinate vector into a deformation field; which converts the canonical map into the corresponding protein conformation. The unknown model parameters include the canonical 3D map, the parameters of the flow generator, and the latent coordinate vector for each particle image. These parameters can be jointly learned from the input images by performing gradient-based optimization.

Referring now to FIG. 1, a system 100 for reconstruction of three-dimensional structure and three-dimensional motion of a protein molecule, in accordance with an embodiment, is shown. The system 100 can be executed on a suitable computing device; for example, a desktop computer, a laptop computer, a server, or the like.

FIG. 1 shows various physical and logical components of an embodiment of the system 100. As shown, the system 100 has a number of physical and logical components, including a central processing unit ("CPU") 102, random access memory ("RAM") 104, an input interface 106, an output interface 108, a network interface 110, non-volatile storage 112, and a local bus 114 enabling CPU 102 to communicate with the other components. CPU 102 executes various modules 120, as described below in greater detail. RAM 104 provides relatively responsive volatile storage to CPU 102. The input interface 106 enables an administrator or user to provide input via an input device, for example a keyboard and mouse. The output interface 108 outputs information to output devices, such as a display and/or speakers. The network interface 110 permits communication with other systems, such as other computing devices and servers remotely located from the system 100, such as for a typical cloud-based access model. Non-volatile storage 112 stores computer-executable instructions for implementing the modules, as well as any data used by these services. Additional stored data can be stored in a database 116. During operation of the system 100, the modules and the related data may be retrieved from the non-volatile storage 112 and placed in RAM 104 to facilitate execution.

In an embodiment, as described in more detail in the following, the system 100 includes various modules 120; including an inputs module 122, a reconstruction module 124, and an output module 126. In further cases, the functions of some or all of the various modules 120 can be combined or performed on other modules, or can be performed on dedicated pieces of hardware. In some cases, some or all of the various modules 120 can be executed on a server-side device 32 or a client-side device 26 (shown in FIG. 2), and be in communication with the other modules. An imaging system 130 may further be linked to the system 100 to obtain cryo-EM images. The imaging system 130 generally comprises one or more electron microscopes, or other suitable devices.

Figure 2:
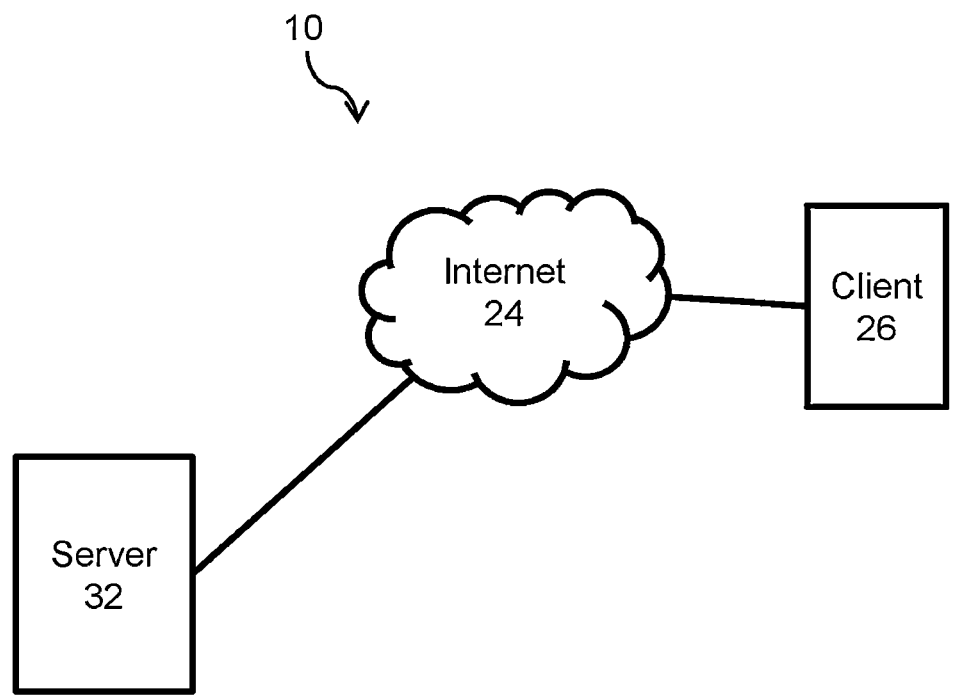
FIG. 2 shows a computing environment of the system of FIG. 1.

In some cases, as shown in a diagram of a computing environment 10 in FIG. 2, the system 100 can communicate with, and retrieve data, from other computing devices; for example, from the server 32 to the client computing device 26. The system 100 can communicate with these devices over a data communication network; for example, the Internet 24.

Figure 4:
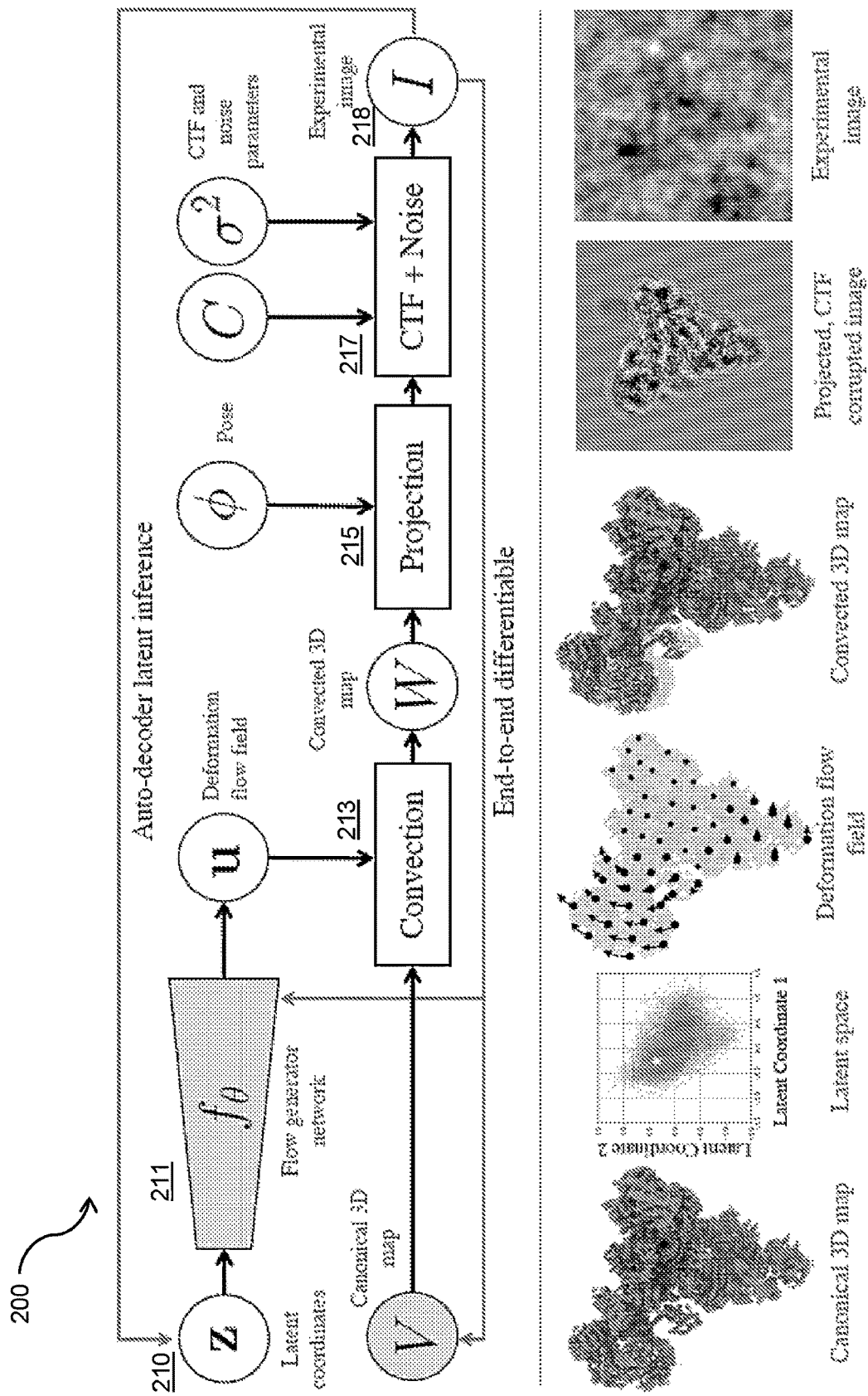
FIG. 4 illustrates an example of a model to determine flexible 3D structure of a protein as deformations of a single canonical 3D density map.

Turning to FIG. 4, shown is a flowchart for a method 200 to simulate the formation of cryo-EM images containing three-dimensional structure and three-dimensional motion of a protein molecule, in accordance with an embodiment. The method 200 can be referred to as 'image formation'.

FIG. 4 illustrates an example of image formation in the 3DFlex model that models the flexible 3D structure of a protein as deformations of a canonical 3D density map V. Under the model, a single particle image is associated with a low-dimensional latent coordinate z that encodes the particular conformation for the particle in the image. A neural flow generator network $f_\theta$ converts the latent coordinate into the flow field u and a convection operator then deforms the canonical density to generate a convected map W. It can then be projected along the particle viewing direction, and contrast transfer function (CTF)-corrupted to generate a simulated image. The simulated image can be compared against the experimental image.

At block 210, the inputs module 122 receives K-dimensional latent coordinates $z_i$ of a particle under investigation in a received cryo-EM image. The cry-EM image can be received from the database 116, the network interface 110, or the imaging system 130 via the input interface 106.

At block 211, the inputs module 122 feeds the latent coordinates $z_i$ to a flow generator $f_\theta(z_i)$ of the reconstruction module 124. This provides a 3D deformation field, denoted u(x), where x is a 3D position and θ denotes the parameters of the generator.

At block 213, the deformation vector field and a canonical 3D density V are input by the reconstruction module 124 to a convection operator, denoted $D(u_i, V)$, which outputs a convected density, denoted $W_i$.

At block 215 and block 217, the reconstruction module 124 then determines a 2D or 3D simulated particle image $I_i$ as a contrast transfer function (CTF)-corrupted projection of plus additive noise η; i.e.:

$$I_i = C_i P(\phi_i) W_i + \eta \qquad (1)$$
$$= C_i P(\phi_i) D(f_\theta(z_i), V) + \eta$$

Here, $C_i$ denotes the CTF operator and $P(\phi_i)$ is the projection operator for the pose $\phi_i$, which specifies the transformation between the microscope coordinate frame and the coordinate frame of the canonical map. The output of this block 217 is a simulated image, to be compared, at block 218, with an experimental image.

Figure 3:
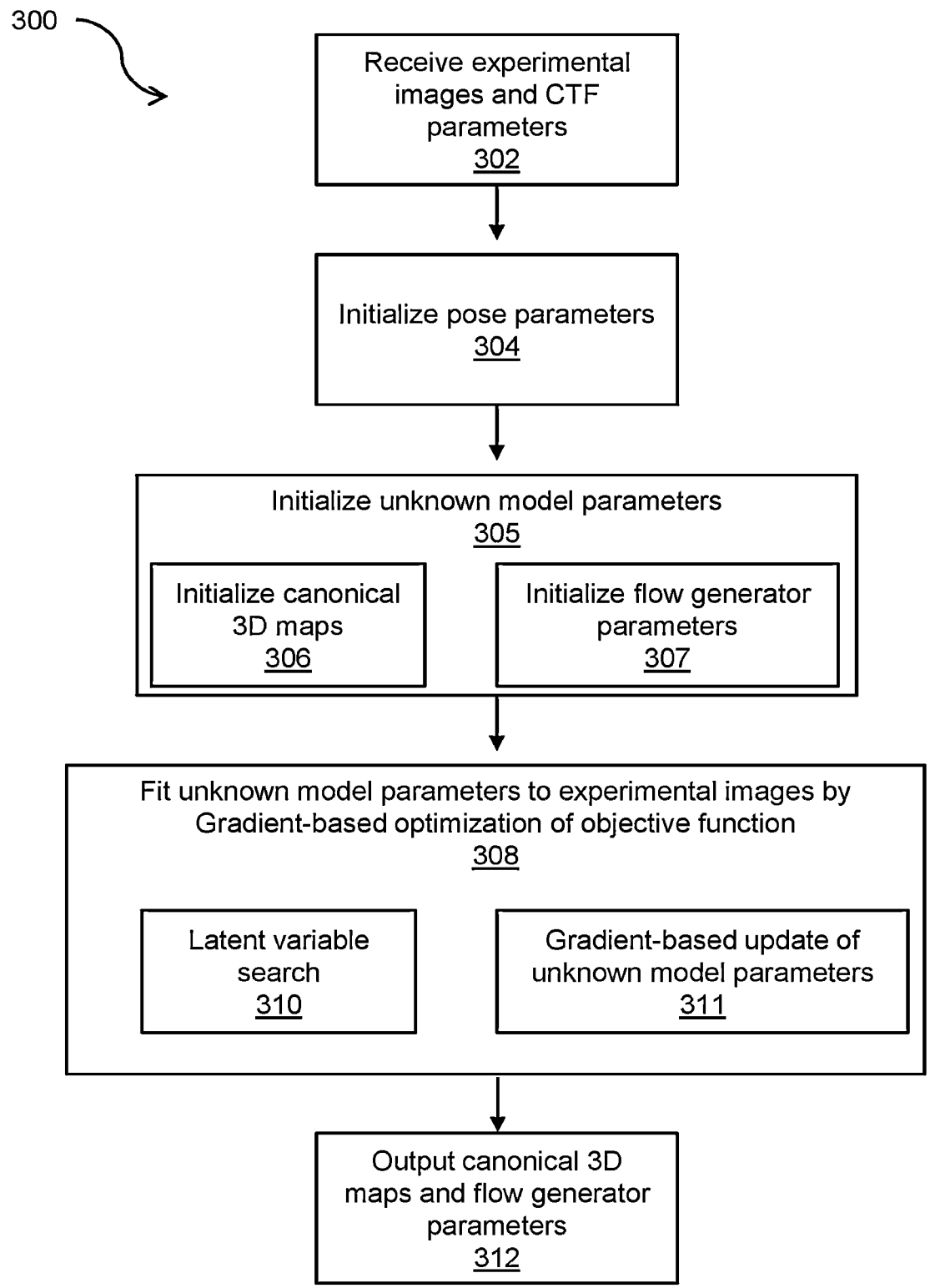
FIG. 3 shows a method for reconstruction of three-dimensional structure and three-dimensional motion of a protein molecule, according to an embodiment.

Turning to FIG. 3, shown is a flowchart for a method 300 to reconstruct the three-dimensional structure and three-dimensional motion of a protein molecule from input experimental images. At block 302, the input module 122 receives experimental images and CTF parameters. Experimental images and CTF parameters can be received from an imaging system 130 via the input interface 106, the database 116, and/or the network interface 110. At block 304, the reconstruction module initializes pose parameters for each experimental image. At block 305, the reconstruction module initializes unknown model parameters; including, at block 306, initializing canonical 3D maps and, at block 307, initializing flow generator parameters. At block 308, the reconstruction module 124 fits the unknown model parameters to experimental images by optimizing an objective function. As described herein, this fitting at block 308 includes, over one or more iterations, at block 310, a latent variable search and, at block 311, a Gradient-based update of unknown model parameters. In an embodiment, the optimization optimizes the flow generator parameters θ, the canonical 3D map V, and the latent coordinates $z_i$, in order to maximize the likelihood of the experimental data under the probabilistic model of image formation (Equation (1)). This is equivalent to minimizing the negative log-likelihood:

$$E_{data}(V, \theta, z_{1:M}) = \frac{1}{2}\sum_{i=1}^{M} \|I_i - C_i P(\phi_i) D(f_\theta(z_i), V)\|^2 \qquad (2)$$

where M is the number of particle images. For notational simplicity, it can be assumed that it is additive white noise; however the formulation can be extended to handle colored noise as understood by a person of skill in the art. In some cases, it can be assumed that poses $\phi_i$ and CTF estimates are known from input, for example from a standard cryo-EM refinement algorithm, though these both could also be re-optimized. Note that the particular form of the noise and corresponding error function Equation (2) can be changed as suitable because any suitable noise model can be used, or equivalently, any suitable error function defining the data term $E_{data}$ can be used.

At block 312, the output module 126 outputs the canonical 3D map and the flow generator parameters to the output interface 108, the database 116, or the network interface 110. In some cases, it also outputs the latent coordinate vectors for each experimental image. The 3D canonical map contains the reconstructed 3D structure of the protein molecule, and the flow generator parameters contain the reconstructed 3D motion of the protein.

Within the above formulation, there are several important design choices that define the architecture of the model. Solving structure and motion from noisy cryo-EM data is a challenging problem. As such, discussion of the design choices below provides insight into the working model, reflecting the present inventors' extensive experimental iterations to arrive at the present invention.

In a particular case, the reconstruction module 124 can use a fully-connected deep neural network with ReLU activations for the flow generator. The input z is the low-dimensional latent coordinate vector for each image, and the output is a 3D flow field u(x). The number of hidden units per layer and the number of layers are adjustable hyperparameters. The final layer is a linear (without biases or nonlinear activation).

The neural flow generator gives the system 100 the capacity to learn complex, nonlinear deformation fields from data, and the inherent inductive bias of the architecture helps avoid over-fitting. Nevertheless, the data is noisy and the number of network parameters is large. Explicit regularization therefore plays a role in reducing the risk of over-fitting; as described herein. Note that the method described herein is general with respect to the form of the flow generator function. A neural network of any suitable architecture, or any other suitable function approximator with adjustable parameters θ, can be used. In particular, neural implicit functions, where the flow generator function does not output an entire flow field but rather only the flow at a specified input coordinate $u(x)=f_\theta(z,x)$, are another suitable family of flow generators.

The latent space represents a conformational landscape, as different latent positions correspond to different deformations of the canonical map. The system 100 determines a latent state (or embedding) for each input image. In probabilistic terms, given an image I, the goal is to infer the posterior distribution p(z|I), such that the high probability latent states are those for which the flow generator and canonical map explain the image well (i.e., minimizing Equation (2)).

Determining the exact posterior distribution is generally intractable for problems such as those solved by the system 100, so instead the reconstruction module 124 uses approximate inferences. One approach, that can be used in variational auto-encoders (VAE), is so-called amortized variational inference, in which a feed-forward neural network (the encoder) is used to approximate the posterior for any given image; e.g., from the input image it computes the mean and covariance over latent coordinates. This approach has been used by deep-learning based heterogeneity methods. In the present context, the amortized variational inference can be trained with the flow generator and the canonical map to maximize the likelihood of the particle images. This approach is typically fast and stable to train. As with VAEs, it incorporates a prior over latent positions that helps to regularize the structure of the latent space to be smooth, mitigating the risks of over-fitting.

The challenge with amortized inference is that it can be extremely difficult for one neural network to do a good job approximating the posterior. In the context of cryo-EM, the encoder network has to effectively invert the decoder network, requiring information about the protein, its motion, and the image formation process. For example, when the flow generator shifts a particular subunit up or down, the encoder must simultaneously learn the same thing in order to determine the best latent states for a given image. This is difficult given image noise, and the lack of explicit access to the canonical density and the 3D deformation field. In general, amortized inference with an encoder has not been found to be sufficiently precise to resolve high-resolution structure and motion.

An alternative, potentially more accurate approach is to perform inference of latent coordinate vectors by applying variational optimization individually for each input image. This entails M optimization problems, in each case finding the optimal approximate posterior over latent coordinate vectors for each experimental image. The task of each optimization problem is to find latent coordinate vectors that, through the image formation process, produce simulated images that are similar to the experimental image (i.e. minimizing Equation (2)). Herein, each of these optimization problems is referred to as latent variable search. Latent variable search takes as input the experimental image and uses the image formation process to infer one or more inferred estimates of the latent coordinate vector associated with this experimental image. Although computationally more expensive than amortized inference with an encoder network, inference by latent variable search is more precise and learning naturally incorporates information across images and viewing directions, capturing structure and motion with sufficient fidelity to resolve flexible protein regions to higher resolution than other approaches.

The use of latent variable search is characterized by the use of the image formation process to measure the similarity of simulated images against the experimental image, and to use this similarity measurement to find latent coordinate vectors that optimize the similarity. This contrasts with methods that use an encoder (such as the VAE) where inference does not involve performing image formation and is instead done in a separate predictive step. Multiple different types of latent variable search can be used in embodiments of the present method, an illustrative selection of which are described herein. The similarity measure of simulated and experimental images used in latent variable search can also vary. In some embodiments, the similarity measure can be chosen to be the same as the negative log-likelihood in Equation (2).

In some embodiments, latent variable search can use an auto-decoder model, in which it directly optimizes a point estimate of the latent coordinate vector for a given image, taking advantage of the structure of the generative model. This entails performing latent variable search by individually optimizing the latent coordinate vector for each experimental image so as to explain the experimental image well (i.e. minimizing Equation (2)). It can also be viewed as variational inference with a Gaussian variational family in the limit as the variance tends to 0.

Because the system 100 uses an end-to-end differentiable generative model, it can compute gradients of the data likelihood with respect to the latent coordinate vectors for each image, and then use gradient-based optimization in order to perform latent variable search. When the dimensionality K of the latent space is small enough, it is also possible to use coordinate-descent in order to perform latent variable search. The latter approach was found to be simpler and equally effective in the experiments.

One benefit of explicitly modeling the posterior distribution p(z|I), rather than a point estimate for $z_i$ given $I_i$, is that the learned latent representations are often more meaningful. As with VAE training, the likelihood of the observed images should be conditioned on samples from the posterior. Uncertainty in p(z|I) means that samples of z in the vicinity of the mean should yield accurate reconstructions of the data. This tends to regularize the model, encouraging smoothness of the latent representation.

While such regularization does not occur naturally with a point estimate of $z_i$, there is a heuristic that produces a similar positive effect, by directly adding noise to the point estimate during latent variable search. This can be likened to variational inference with a Gaussian variational family with a fixed covariance, and can be used to regularize deterministic auto-encoders. The reconstruction module 124 lets the variance of the injected noise be determined by the distance of a given latent point to other nearby embedded points. In addition to noise injection, the reconstruction module 124 can use a Gaussian prior on latent coordinates with unit variance to help control the spread of the latent embedding for a given dataset, and to center it at the origin in the latent space.

Note that for the method described herein, noise injection and the particular prior over latent coordinates are not strictly necessary. The method can use any suitable technique for smoothing the latent space and accounting for uncertainty in latent inference. For example, it is suitable to compute multiple samples from the posterior and use an importance sampling or variational method to draw samples from the resulting approximation to the posterior in order to perform latent variable search.

Algorithms for single-particle reconstruction commonly represent 2D and 3D maps and 2D and 3D images in the Fourier domain. This reduces the computational cost of the CTF-corruption operation and image projection (via Fourier-slice theorem). It also allows maximum-likelihood 3D reconstruction with known poses in closed-form, as is familiar to those skilled in the art. On the other hand, the convection of density between conformations is more naturally formulated as a real-space operation. Features and structures in the canonical density map V need to be shifted, rotated, and potentially deformed to produce densities consistent with the observed particles.

The reconstruction module 124 can represent the canonical map V in real-space, as a voxel array of size $N^3$. Convection and projection can be performed in real-space, and in practice are combined into a single operator that does not store $W_i$ explicitly. Once the projected image of the convected map is formed, it is transformed to Fourier-space, CTF-corrupted, and transformed back to real-space to be used with the observed image for likelihood computation. Interestingly, the reconstruction module 124 can also find that 3D reconstruction of the high resolution canonical map is also possible in real-space using suitable optimization techniques. Computationally, real-space convection and projection are far more expensive than Fourier-space slicing, and the FFT for CTF modulation must be applied for every image in the forward pass, and also in the backwards pass for computing gradients. Nevertheless real-space reconstruction is effective, as demonstrated herein.

Note that any suitable representation of the canonical map can be used. The present disclosure uses a real-space representation but it is equally appropriate to use any other representation. For example, neural implicit functions that model the density as a function of spatial position $V(x)=g_\psi(x)$ where g is a neural implicit function and $\psi$ are it's parameters. Any other representation can be used, for example a wavelet basis, or a learned or optimized basis.

Convection of density is used to model the physical nature of protein motion, thereby allowing high-resolution structural detail from experimental data to backpropagate through the model. There are several ways to construct a convection operator. One way is to express the flow field as a mapping from convected coordinates (i.e., of voxels in $W_i$) to canonical coordinates. Convection then requires interpolating the canonical density V at positions specified by the flow field. However, in order to maintain conservation of mass the interpolated density must be modulated by the determinant of the Jacobian of the mapping, which can be challenging to compute and differentiate.

Instead, the flow, $u_i(x)$, represents a forward mapping from canonical coordinates in V to the deformed coordinates in $W_i$. This naturally conserves density, as every voxel in V has a destination in $W_i$ where its contribution is accumulated through an interpolant function. The convected density at x can be written as:

$$W_i(x) = \Sigma_y k(x - u_i(y)) V(y) \quad (3)$$

where $u_i = f_\theta(z_i)$, and $k(x)$ is an interpolation kernel with finite support. In this case, divergence and convergence of the flow field must be treated carefully to avoid undesirable artifacts such as holes, Moiré patterns, and discontinuities. It was determined to be advantageous to use high-order (e.g., tricubic) interpolation and strong regularization (described herein) to ensure accurate interpolation and artefact-free gradients.

Note that any suitable convection operator, that can be differentiated, can be used.

As capacity is added to the model, the propensity for over-fitting becomes problematic without well designed regularization. Over-fitting can result in the formation of localized, high-density points ("blips") in the canonical map, along with flow fields that translate these aberrations by large distances to explain noise in the experimental images. This can be especially pronounced with smaller proteins, higher levels of image noise, and membrane proteins containing disordered micelle or nanodisc regions (i.e., structured noise). Over-fitting also occurs when the regularization is not strong enough to force the model to separate structure from motion. For example, rather than improve the canonical density with structure common to all conformations, the model sometimes learned to deform a low-resolution canonical density to create high-resolution structure (with highly variable local deformations).

To address such issues, the reconstruction module 124 exploits prior knowledge of smoothness and local rigidity in the deformation field. In particular, it is unlikely that natural deformations would involve large discontinuities in regions of high density; e.g., an α-helix should not be sheared into disjoint pieces. It is also unlikely that formations will be highly non-rigid at fine scales in regions of high density; at the extreme, bond lengths should not stretch or compress substantially. While simple regularizers can be used, like limiting the frequency content of the flow field, or penalizing its curvature, these are difficult to tune and do not prevent over-fitting reliably.

The reconstruction module 124 can instead model flow generation using finite-element methods. A tetrahedral mesh covering regions of high density is generated in the canonical frame, based on a preliminary consensus refinement. The deformation field is parameterized by a 3D flow vector at each vertex of the tetrahedral mesh. The deformation field is then interpolated using linear FEM shape functions within each mesh element. Smoothness is enforced implicitly through interpolation as a function of the size of the mesh elements, which is an adjustable parameter, and the fact that adjacent elements share vertices.

Local rigidity of the flow is also encouraged in each mesh element. In more detail, the deformation field within the jth tetrahedral element for image i, denoted $u_{ij}(x)$ can be written as a linear mapping:

$$u_{ij}(x)=A_{ij}x+b_{ij} \quad (4)$$

where matrix A and vector b are uniquely determined from 3D flow vectors at the element vertices. Local non-rigidity is quantified in terms of the distance between A and the nearest orthogonal matrix (in a MSE sense). In particular, the reconstruction module 124 measures the squared deviation of the singular values of A from unity. Letting $s_{ij}$ $s_{ij}^\ell$ be the $\ell$ th singular value of $A_{ij}$, we express the local rigidity regularization loss as:

$$E_{rigid}=\Sigma_i\Sigma_j w_j \sum_{\ell=1}^{3}(s_{ij}^\ell-1)^2 \quad (5)$$

where $w_j$ are weights defining the strength of the prior within each mesh element, based on the density present within the jth mesh element. The densest elements have weight 1. Empty elements have weight 0. This ensures that deformation fields are permitted to compress and expand empty space around the protein.

Note that for the method described herein, regularization using a tetrahedral mesh is not the only suitable regularization. Other regularizers can be used, such as those that limit the Fourier-space content of deformation fields, penalize curvature, divergence, and/or curl of the deformation fields. It is also suitable to use any other regularizer, for example a learned regularizer that computes the penalty as the output of a particular function on deformation fields. For example, a suitable regularizer may use an atomic or pseudoatom model of the target protein to define regions that should be continuous and rigid and interfaces where shear, expansion, and contraction can be allowed. The regularizer may be in the form of a penalty or direct constraints on the flow generator network. The regularizers may operate on any or all of the variables, including the canonical density, the flow generator, and the latent variables.

Image formation 200 is end-to-end differentiable, so in reconstruction method 300, at block 308, gradient-based optimization can be used to optimize the unknown model parameters of the flow generator the canonical map that best explains the experimental images. Any type of gradient-based optimization that uses the gradient to compute and apply an update to the parameters can be used. It may be advantageous to use either Adam or Stochastic Gradient Descent (SGD) with Nesterov acceleration, with mini-batches of size at least 500 because of the high levels of image noise. In a given iteration of gradient-based optimization, inference of the latent coordinate vectors (i.e. latent variable search) for each experimental image in a minibatch can be performed prior to computing gradients with respect to the canonical density and flow parameters, or values of inferred latent coordinate vectors from previous iterations or initialization can be used prior to computing the gradients, or only latent variable search can be performed and gradient-based updating can be skipped in some iterations. The loss function being optimized in gradient-based optimization can be a weighted sum of the data log likelihood (Equation (2)) and the non-rigidity penalty (Equation (5)):

$$L=E_{data}+\lambda_{rigid}E_{rigid} \quad (6)$$

During optimization, the reconstruction module 124 can use spatial frequency matching, learning the model in a coarse-to-fine manner. The canonical density V is constrained to be low-pass, with an upper frequency band-limit which increases over iterations. The frequency and learning rate schedule, and $\lambda_{rigid}$, must be tuned for each dataset in our current implementation. Optimization is done with a box size, $N=N_L$, that is typically smaller than the raw size of the particle images, i.e., $N_H$. As such, optimization only uses information below the Nyquist frequency for the smaller box size, and therefore is limited in spatial frequency to a lower limit. Optimization can also be run at the full box size, therefore being limited to a higher spatial frequency limit. During optimization, it is also possible to apply a real-space mask to the flow generator output to ensure the deformation is zero except in a region of interest; e.g., to exclude motion of a micelle or nanodisc.

To initialize training, the canonical density V can be set to be a low-pass filtered version of a consensus refinement given the same particles or can be initialized from another suitable source. The parameters of flow generator can be randomly initialized. The latent coordinates for the particles are either initialized to zero or to the output of another heterogeneity embedding method. In some experiments, especially on smaller, low SNR particles, it was determined that initializing with latent coordinates from 3D Variability Analysis (3DVA) in cryoSPARC improves results.

It was determined that simultaneously training of the canonical density V and flow generator parameters θ leads to over-fitting after thousands of gradient iterations, despite strong regularization. In these cases, V and θ can be initially trained with latent coordinates $z_i$ fixed to their initial values from 3DVA for 5 epochs. Then, the latent coordinates are unlocked and latent inference is performed for each minibatch while updating θ, but with V fixed, for 10 epochs. Then, alternating updating V with θ fixed for 10 epochs, and repeated until convergence. In general, any schedule of optimizing some variables while holding others fixed is suitable.

With the ability of the system 100 to capture detailed motion and precise latent coordinates of particle images, it becomes possible in principle to recover high resolution detail of the flexible parts of protein molecules that move, that would otherwise be blurred in standard reconstruction results. In some cases, "focal" reconstructions can be used, where a particular focal point in 3D space is chosen, and for each particle image, the flow $u_i=f_\theta(z_i)$ is approximated by a local rigid transform around the focal point. The local rigid transform, given by a rotation and shift, is composed with the overall pose of the particle $\phi_i$ to arrive and a new "focal" pose for each image. The particle images are then subject to standard Fourier-space reconstruction from these updated poses, and the result is a 3D density map where the flexible motion around the focal point has been corrected, and local density may be improved. Focal reconstructions can be repeated at many focal points covering the protein molecule, and the resulting maps stitched together. However, this approach is generally tedious and encounters issues when there is any curvature or non-rigidity in the flow fields.

As discussed herein, one can reasonably assume that the deformation flow fields will be smoother than the high resolution canonical map. Accordingly, the entire model can be optimized at a small box size, $N=N_L$. Once optimization is complete, the flow generator parameters θ and the latent coordinates $z_i$ can be 'frozen', and then transferred to a new model at full resolution, with $N=N_H$. The particles can be partitioned using the same split that was used in the consensus refinement (from which three poses $\phi_i$ are obtained). For each half-set, the canonical density V is initialized to zero, and re-optimized at full box size $N_H$. This yields two half-maps that can be compared via Fourier-Shell Correlation (FSC). In this way, any FSC correlation beyond the Nyquist limit at box size $N_L$ represents true signal recovered in common in both half-maps that was never seen during training. As a consequence it cannot be spurious or a result of over-fitting.

To this end, the system 100 optimizes V at high resolution under the full model using the same optimization procedures described herein. In some cases, using minibatch SGD was found to not yield high quality results. One can speculate that noise in the minibatch gradient estimator is problematic for this task. Nevertheless, the present inventors were able to solve the problem using full-batch gradient-based optimization using the Limited-memory-Broyden-Fletcher-Goldfarb-Shanno (L-BFGS) gradient-based optimization method. This is generally more computationally expensive than direct Fourier-space reconstruction, and requires many iterative passes over the whole dataset. But it is notable that the present inventors were able to obtain high quality results in this way. In particular, this approach solves high resolution detail in all flexible parts of the protein molecule simultaneously, without making assumptions of local rigidity or smoothness, validated with FSC.

The present inventors conducted example experiments where the application of the system 100 to two experimental cryo-EM datasets was examined. The experiments demonstrated the ability of the method to resolve multiple dimensions of non-linear non-rigid protein motion with sufficient fidelity to improve reconstruction resolution of flexible parts. The first dataset contains snRNP spliceosome particle images, and the second contains TRPV1 ion-channel particle images.

For each dataset, a rigid consensus refinement was computed using all particle images. Non-uniform refinement is used to improve image alignments and overall resolution. The resulting particle images and poses $\phi_i$ are fixed and used in training the model of the present embodiments. No prior information is provided about the type or form of heterogeneity in each dataset. The system 100 was run with a real-space mask that excludes solvent in the canonical density V, and for membrane proteins a separate mask is used to enforce zero deformation of detergent micelle or lipid nanodisc. For the TRPV1 channel, 3D Variability Analysis (3DVA) was first run on the particle images to generate initializations for latent coordinates $z_i$, again without any prior information about heterogeneity. Each experiment was run on a single NVIDIA™ V100 GPU.

To display continuous motion results as static figures, multiple points $Z_{display}$ in the latent space of the model are selected and the corresponding convected densities as $W_{display} D(f_\theta(z_{display}),V)$ are generated. These densities can be rendered overlayed in multiple colors and with reference position guide markers to aid the visibility of motion.

The U4/U6.U5 tri-snRNP complex represents a large part of the spliceosome and is a molecular machine that has several moving parts, linkages, and flexible domains. The example experiments processed a dataset of 138,899 snRNP particles (EMPIAR-10073). The raw particles had a box size of 380 pixels and a pixel size of 1.4 Å and were first processed through heterogeneous refinement in cryoSPARC software to separate broken particles that are missing the "head" region. This yielded 102,500 final particles that are downsampled to a box size of 180 pixels (pixel size 2.95 Å) and used to train the model. The original raw particles are then input to the system described herein and used to reconstruction the canonical density (in two separate half-maps) to high resolution, once the system 100 has learned the motion.

The system 100 was trained starting from random initialization for latent coordinates and the flow generator network, with a K=5 dimensional latent space. The flow generator was a 6-layer MLP with 64 units in each hidden layer and output layer, using ReLU activations. A tetrahedral mesh with 1601 vertices and 5859 cells is created, covering the density, and the flow generator outputs the deformation field at these vertices.

The system 100 recovered five dimensions of latent motion (illustrated in FIG. 5), with each dimension explaining a different type of bending or twisting in the molecule. There are two large moving parts, the head region and foot region. Both are attached to the more rigid central body region. In the learned deformation fields from 3DFlex, the foot region largely moves as a rigid sub-part, with a hinge-like linkage to the body. The head region has significant internal flexibility and a large range of motion, and all five latent directions encode some motion in the head region. Notably, the system 100 recovers the motion of all regions from a random initialization without any labels defining parts or linkages.

Figure 5:
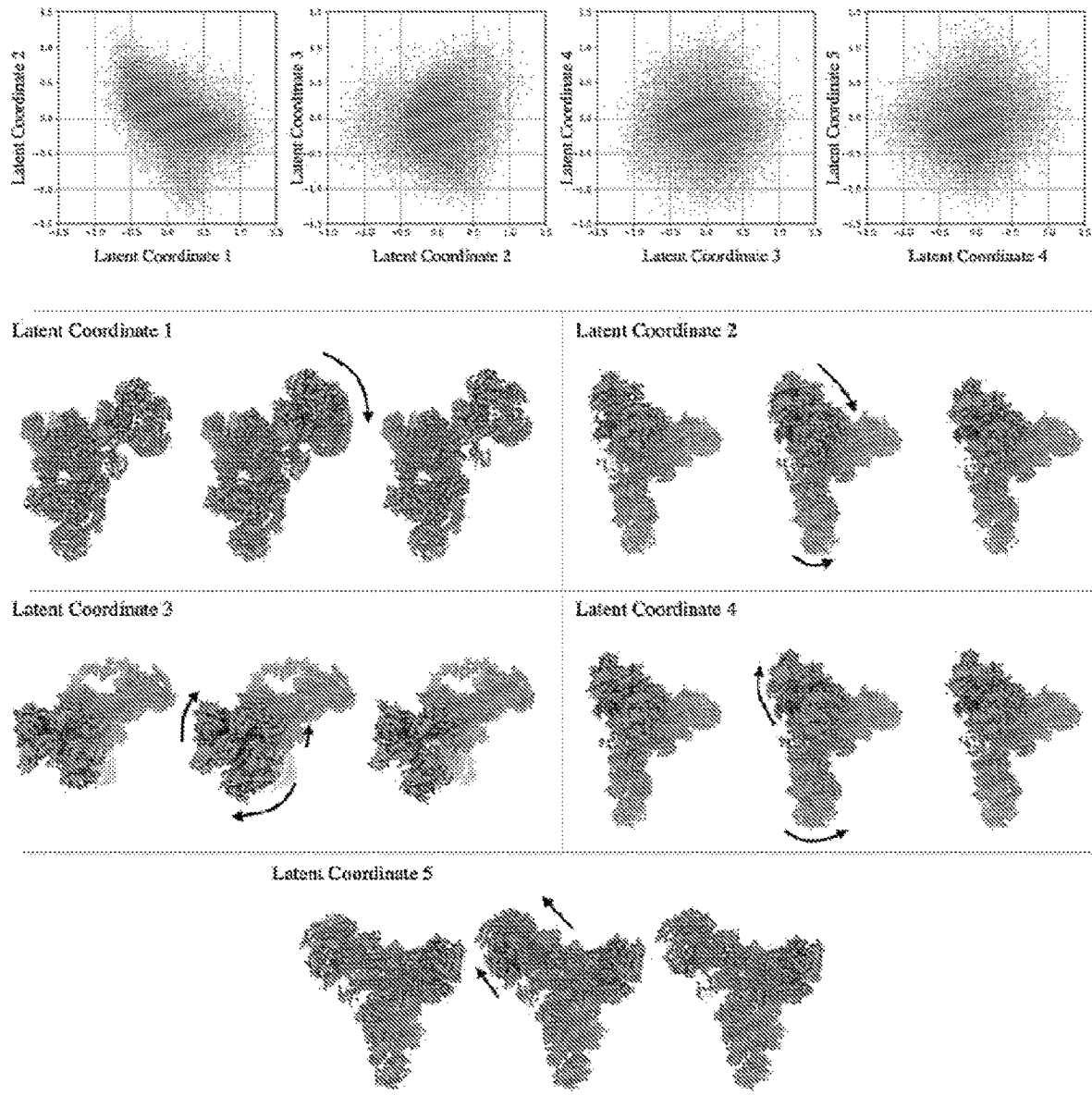
FIG. 5 illustrates experimental results of the system of FIG. 1 with a K=5-dimensional latent space on 102,500 particles of an snRNP Spliceosome complex

FIG. 5 illustrates results of the system 100 with a K=5-dimensional latent space on 102,500 particles of an snRNP Spliceosome complex, demonstrating the capacity for the system 100 to resolve multiple modes of non-rigid deformation simultaneously. Shown are scatter plots showing the final distribution of particle latent coordinates across the dataset and convected densities from the system 100 at minus one and plus one standard deviations in the latent space, along each of the five latent dimensions. Each dimension resolves a different type of motion within the same model.

Figure 6:
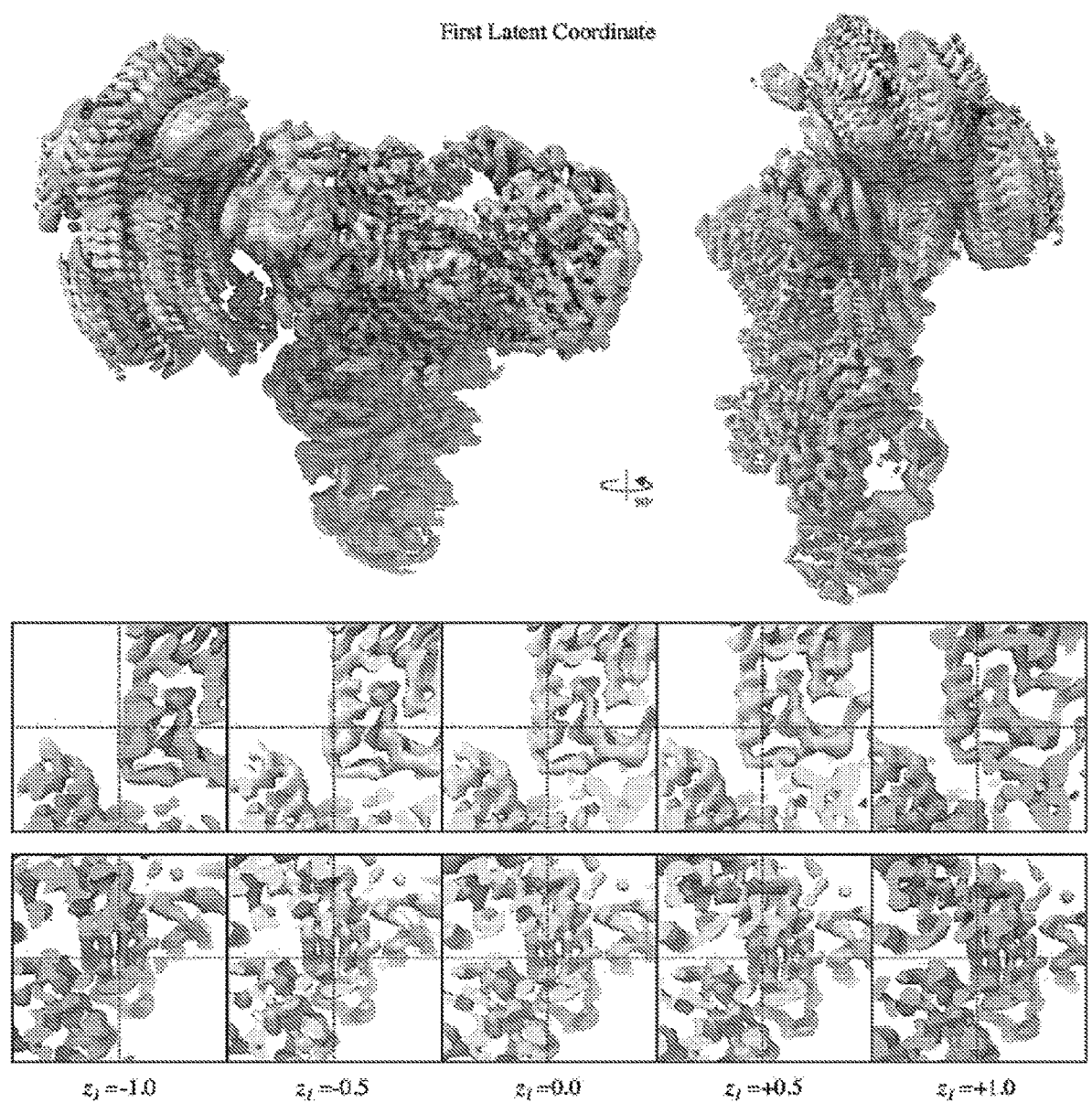
FIG. 6 illustrates experimental results of the system of FIG. 1 on 102,500 particles of an snRNP Spliceosome complex.

Along with the motion, the system 100 was able to recover high-resolution detail in the canonical density map (illustrated in FIG. 6). Individual α-helices can be seen translating several Angstroms while retaining side-chain features. Likewise, a β-sheet in the flexible head region is sufficiently resolved to separate β-strands, despite the presence of non-rigid motion. The system 100 only had access to experimental data at a maximum Nyquist resolution of 5.9 Å during training, and so these structural features represent additional signal that is resolved from the data due to precise modelling of the motion.

FIG. 6 illustrates results of the system 100 on 102,500 particles of an snRNP Spliceosome complex, demonstrating the capacity for the system 100 to resolve detailed non-rigid motion and high-resolution structure simultaneously. Shown are a series of convected densities from the model, at latent coordinates along the first latent dimension, and with focus on key structural details. The top row shows an α-helix in the head region of the protein that translated by several Angstroms and the bottom row shows a β-sheet in the head region that translates and deforms.

Figure 7:
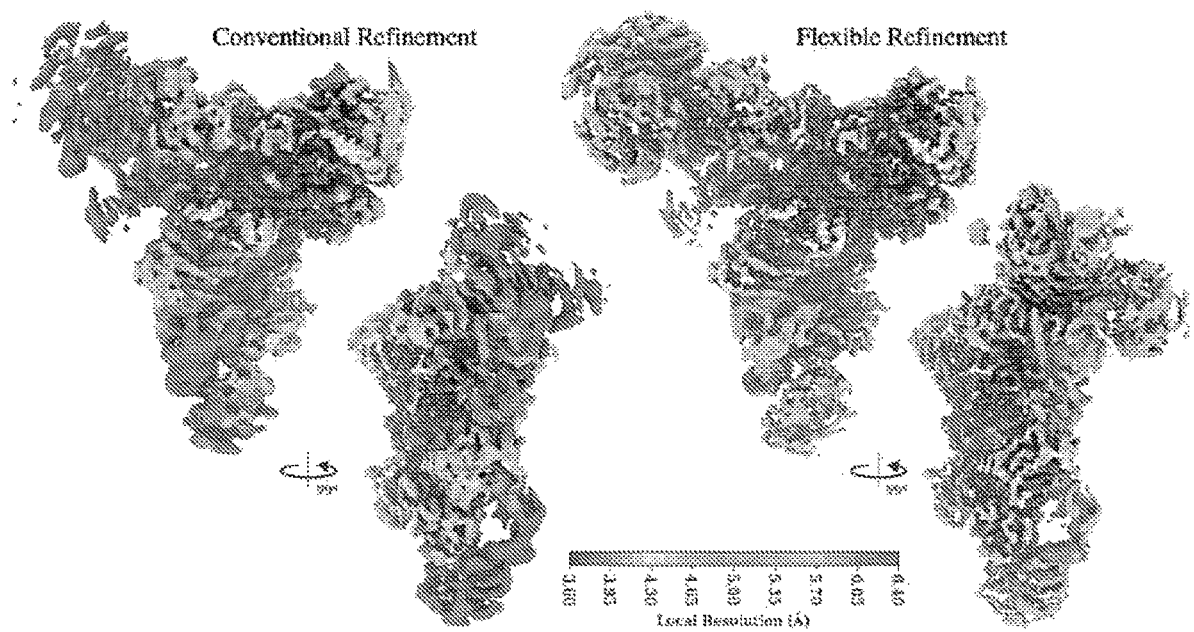
FIG. 7 illustrates experimental results of the system of FIG. 1 with a K=5-dimensional latent space on 1002,500 particles of an snRNP Spliceosome complex.

As expected, in regions of substantial motion and flexibility, improvements between a static conventional refinement and the system are dramatic (illustrated in FIG. 7). For example, local resolution in the center of the head region is improved from 5.7 Å to 3.8 Å. For a complex as large as the snRNP, it is possible to create manual masks around regions that are expected to be rigid and then to perform local or multi-body refinement. These techniques can improve resolution and map quality in some domains, such as the foot region, that remain rigid despite motion relative to the remainder of the molecule. In contrast, the system 100 does not require any manual masking or prior knowledge about the motion of the molecule. It can detect and then correct for non-rigid flexibility across the entire molecule at once.

FIG. 7 illustrates results of the system 100 with a K=5-dimensional latent space on 1002,500 particles of an snRNP Spliceosome complex. On the left is a density map from conventional refinement. On the right is a canonical density map from the system 100. The two maps are filtered by local resolution to aid in visualizing weak density in low resolution areas in the conventional refinement.

The TRPV1 ion channel is a 380 kDa tetrameric membrane protein that acts as a heat- and capsaicin-activated sensory receptor. A dataset of 200,000 particle images of TRPV1 in nanodisc (EMPIAR-10059) with a box size of 224 pixels and pixel size of 1.21 Å was processed. These particles were downsampled to 128 pixels (pixel size 2.15 Å) and used to train the system 100. The original raw particles were then used to reconstruction the canonical density (in two separate half-maps) to high resolution, once the system 100 had learned the motion.

The experiments first ran 3D Variability Analysis with K=2 components. This provides initialization for K=2 latent coordinates $z_i$. The flow generator, a 3-layer MLP with 32 units in each hidden and output layer, was randomly initialized. The system 100 was trained for 5 epochs over the data with the latent coordinates fixed. The latents were then unlocked and were optimized at each iteration. Training proceeded for 10 epochs at a time, alternating between fixing the canonical density and fixing the flow generator, for a total of 50 epochs.

Figure 8:
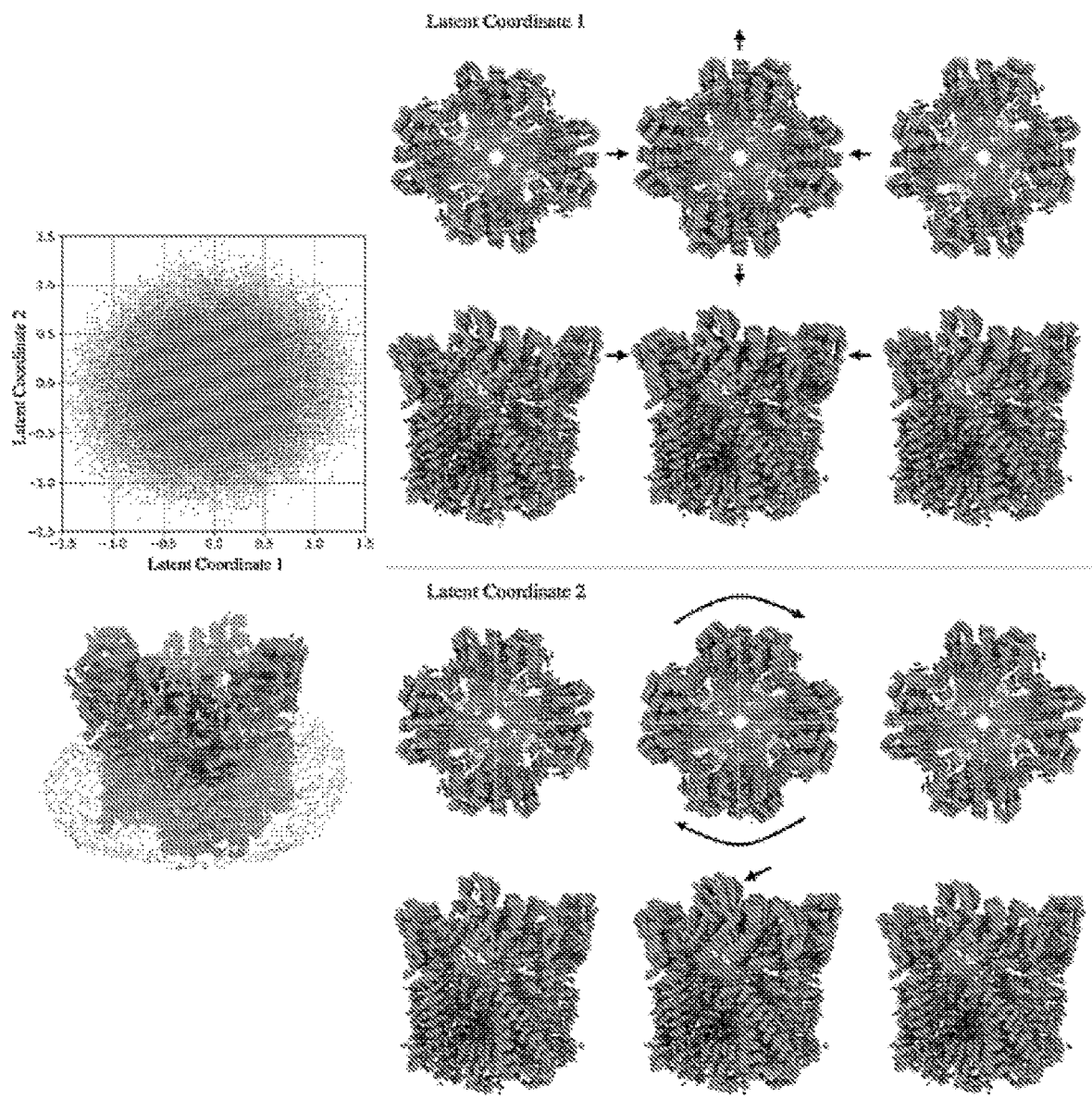
FIG. 8 illustrates experimental results of the system of FIG. 1 with a K=2-dimensional latent space on 200,000 particles of a TRPV1 ion channel protein.

The final result is a model that has captured K=2 types of flexible coordinated motion amongst the four peripheral soluble domains of the ion channel (illustrated in FIG. 8). Along the first latent dimension, each pair of opposing subunits bends towards each other while the other pair bends apart. The second motion involves all four subunits twisting concentrically around the channel's pore axis. In both cases, the peripheral-most helices move by approximately 6 Å. Both motions are non-rigid and involve flexure of substantial regions of the protein density.

FIG. 8 illustrates results of the system 100 with a K=2-dimensional latent space on 200,000 particles of a TRPV1 ion channel protein, demonstrating the capacity to resolve detailed motion of smaller, membrane proteins. Shown are scatter plots showing the final distribution of particle latent coordinates across the dataset. Also shown are canonical density that is solved by the system 100. The micelle is not excluded in the density but is masked to have zero deformation, so that the system 100 focuses on motion of the protein density. Also shown are convected densities from the system 100 at minus one and plus one standard deviations in the latent space, along each of the two latent dimensions. The first dimension resolves a motion where opposite soluble domains move together or apart. The second dimension resolves a motion where all four soluble domains twist around the axis of the central pore.

Figure 9:
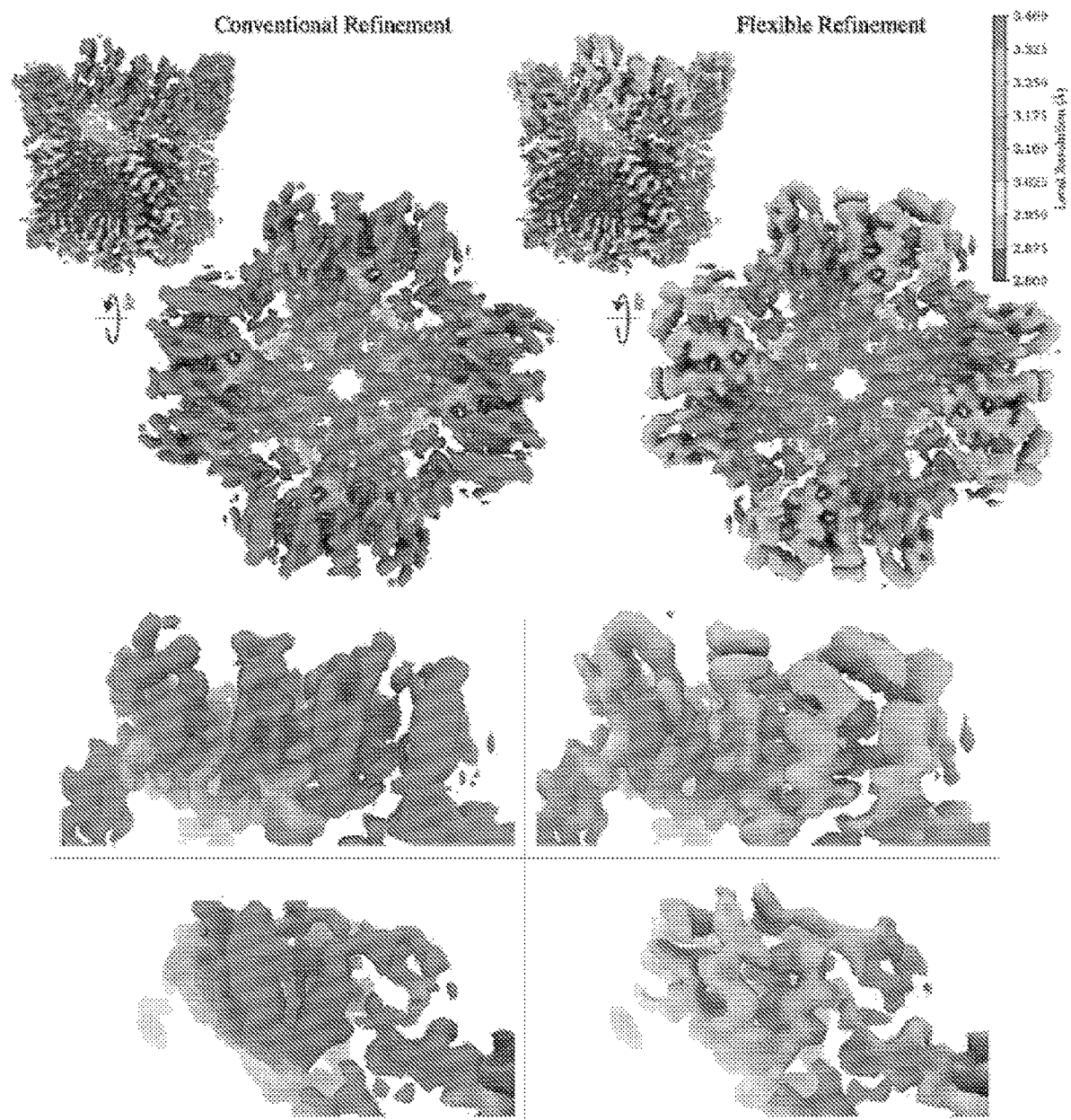
FIG. 9 illustrates experimental results of the system of FIG. 1 with a K=2-dimensional latent space on 200,000 particles of a TRPV1 ion channel protein.

In a conventional refinement of the TRPV1 channel structure, these motions are detrimental to reconstruction quality and resolution (illustrated in FIG. 9). Several α-helices in the soluble region are so poorly resolved that helical pitch is barely visible. Local resolution reaches 2.8 Å in the rigid core of the channel, but only 4 Å in the periphery. The system 100, on the other hand, estimates and accounts for the motion of these domains, and substantially improves resolution and map quality. The system 100 only has access to experimental data up to a maximum Nyquist resolution of 4.3 Å during training, but FSC and local resolution measurements using the two separate half-set reconstruction show that it recovers consistent structural information beyond this resolution. Local resolutions in peripheral helices improve to 3.2 Å revealing helical pitch and side chain details.

FIG. 9 illustrates results of the system 100 with a K=2-dimensional latent space on 200,000 particles of a TRPV1 ion channel protein. On the left is shown a density map from conventional refinement with local resolution. On the right side is shown canonical density map from the system 100, using the same local resolution scale. The two maps are identically filtered and sharpened and displayed at the same threshold level, so that visual comparison of map quality is possible. The result of the system 100 shows clear improvement in map quality and local resolution in peripheral flexible domains of the protein. Also shown are detailed views showing improvement in helical density in the flexible soluble domains.

Figures 10A, 10B, 10C:
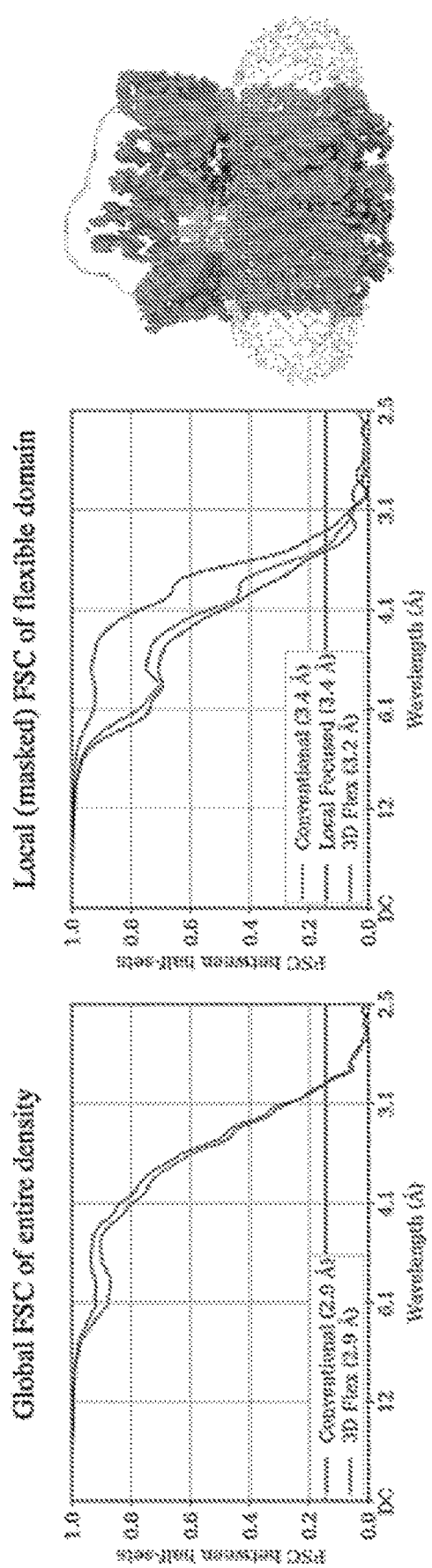
FIG. 10A shows experimental results of a FSC of an entire density of the ion channel of the system of FIG. 1.
FIG. 10B shows experimental results of a FSC using a mask around one of the flexible peripheral domains in the soluble region of the ion channel.
FIG. 10C shows experimental results of a mask in accordance with FIGS. 10A and 10B.

The two separate half-set reconstructions from the system 100 allow for the ability to use established validation procedures to measure the improvement from modelling motion. FIG. 10A shows that the global FSC curve of the entire density improves slightly with the system 100 compared to conventional refinement. This indicates that in the highest resolution rigid core region of the molecule, the system 100 has not lost any structural information. To investigate the effect in the peripheral domains, the experiments constructed a soft-edged mask around one of the flexible domains (shown in FIG. 100). Computing FSC curves within this mask (illustrated in FIG. 10B) shows that the system 100 improves the average resolution from 3.4 Å to 3.2 Å as well as the SNR at lower resolutions. This means that the system 100 has resolved more structural information than conventional refinement for this flexible protein, and validates that the motion learned by the system 100 is a better model of the particle than a null hypothesis of no motion.

FIGS. 10A to 100 show validation and resolution estimation results of the system 100 with a K=2-dimensional latent space on 200,000 particles of a TRPV1 ion channel protein. FSC curves were measured between half-sets of particles that are used to compute two half-map reconstructions. The system 100 only had access to experimental data up to a Nyquist resolution limit of 4.3 Å during training. Therefore, any correlation beyond this resolution in half-set reconstructions indicates resolved signal rather than spurious correlation or over-fitting. FIG. 10A shows a FSC of the entire density of the ion channel, showing that the system 100 resolves high-resolution details in the rigid core of the protein. FOG. 10B shows FSC using a mask around one of the flexible peripheral domains in the soluble region of the ion channel. The mask is depicted in FIG. 100 and is soft-edged. In this region, the system 100 provides a substantially improved FSC curve and resolution estimate of 3.2 Å; versus 3.4 Å for conventional refinement. Notably, a local focused refinement using the same mask is unable to improve resolution beyond the conventional refinement due to the small size and non-rigidity of the flexible region.

The system 100 has improved the reconstruction of this flexible protein by explicitly modelling non-rigid deformation. As a baseline, the experiments also performed a local focused refinement using the same mask (FIG. 100) to isolate one soluble domain. Local refinement is unable to improve the density or resolution of the domain and beyond the conventional refinement. This is expected, as each soluble domain is less than 50 kDa in size and deforms flexibly. It is believed that this comparison illustrates an additional advantage of the system 100. Unlike local and multi-body refinement methods that assume rigidity and attempt to fit separate pose parameters for each masked region, the system 100 can exploit correlations between different moving parts that may move together, making it possible to infer the position of all parts, even though individually each is too small to align reliably. In the case of TRPV1, the four soluble domains deform in different directions by different amounts, but the system 100 infers their positions in a given image jointly.

Advantageously, the system 100 can also be used to model heterogeneity. Discrete heterogeneity is a long-studied form of heterogeneity that can be easily modelled and computed from cryo-EM image data. Discrete models approximate continuous conformational landscapes with a finite number of points as a crude approximation. As such, they cannot aggregate structural information across conformations, and have no notion of flexibility or protein motion. Some recently proposed deep learning methods for heterogeneity attempt to approximate continuous conformational landscapes with finer and more elaborate discrete clustering methods, still without a notion of motion or unifying structural details across conformational space. They require massive datasets due to the partitioning of conformational space into discrete reconstructions.

Local and multibody refinements are another long-studied method to attempt to deal with continuous heterogeneity. Local refinements use masks to cut a 3D protein density into finitely many (usually a small number less than 5) rigid sub-parts that can rotate and/or shift relative to one-another. This approximation to a continuous deformable object can allow for improvement in map quality and resolution, but is only applicable when there are actually rigid substructures, each with enough density to be individually alignable. These methods also require substantial manual interaction to define masks.

Several other methods have been proposed to model continuous conformational heterogeneity using density-based models. The simplest of these, methods based on eigen-analysis, model conformational landscapes as linear subspaces in 3D density. More advanced techniques use non-linear manifold embedding or deep generative models to construct a non-linear manifold in the space of 3D density. These methods do succeed in modelling continuous heterogeneity in the sense that the models are actually continuous, but the models do not have a notion of protein motion. Instead, density-based models are limited to adding and subtracting density from different areas of a 3D structure, and do not aggregate structural information across the landscape or enable improved reconstructions of heterogeneous proteins.

Other methods attempt to model continuous conformational change with an underlying notion of protein motion. Hypermolecules define continuous conformational change by representing protein density using a higher-dimensional space that could, in principle, capture deformation and structure together. This technique is quite different from the architecture of the present embodiments as it does not explicitly separate canonical density and deformation, and it has generally yet to produce notable results on experimental data. Other methods fit a Gaussian Mixture Model (GMM) as a representation of canonical density, and uses a deep generative model to adjust the parameters of the GMM to model continuous conformational change of protein density. While GMM parameters can be adjusted to convect density in modeling motion, the GMM parameters can equally be used to add or subtract density like a density-based model, and no regularization is used to enforce that the model actually learns motion. Furthermore, the deep generative model is a (variational) auto-encoder meaning that a separate encoder network is necessary, unlike the present embodiments where latent variable search is used instead. The encoder network in the GMM model also does not perform inference by operating directly on experimental data, instead it takes as input a gradient of the data likelihood with respect to initial GMM parameters. This means that the encoder is limited to encoding motion that is small relative to the size scale of Gaussians used in the mixture, limiting motion the model can learn to locally linear small motion of high resolution objects, or locally linear large motion of low resolution objects. In contrast, the present embodiments can capture large motion even of high-resolution objects. Finally, due to these limitations and computational limitations, the GMM model does not improve the resolution or map quality of the canonical density.

The present embodiments can also be used in other applications, extensions and variations. For example, in addition to a deformation flow generator, the model can include an additional module that generates a "presence/absence" field that captures the association/dissociation of subunits in a complex. This module would take in the latent coordinate $z_i$ and output one or more masks indicating which parts of the canonical density are present in the i'th particle image. The mask would then be used to multiply the canonical density before deforming through the convection operator. In this way, the model can handle both flexible conformational variability and compositional variability. For instance, this could be helpful when working with a dataset containing a protein and a ligand, or multiple subunits in a complex.

The present embodiments can also be used on multiple different datasets of protein particle images jointly. For example, data can be collected with particles in the presence and absence of a ligand, or at different temperatures, or with different sample characteristics of any kind, or at different times after a reaction has taken place. The data can be combined into one particle stack that is used by the system 100, and the distribution of particles in the latent space can be analyzed with respect to the originating sample conditions. This can be used for example to understand the changes in conformational dynamics after ligand binding or after an enzyme has begun acting on it's substrate.

In some cases, the model can be initialized with latent coordinates or flow generator parameters, or a canonical density, from any source; for example, other algorithms that uncover the conformational landscape.

The latent coordinates output from the system 100 can be used in conjunction with the flow generator to compute "free energy" or related molecular energies to determine the likelihood of a given conformational state.

In some cases, the model can fit initially to image data from one source, for example a low energy, low cost microscope or a microscope set with imaging conditions that maximize low/mid-resolution contrast at the expense of high-resolution contrast. Once the model is trained on this data, it can then be fine-tuned on a different source of image data, for example high-energy high-cost microscope data, or data from a microscope set to maximize high-resolution information at the expense of low/mid-resolution information, or from data collected with minimal radiation damage, or from data of a different target sample (e.g. with or without a ligand).

In some cases, the model can be extended to support particles with various geometries, sub-units, symmetries, and connected parts by expanding the generative architecture to have multiple canonical maps and multiple flow generators. In some uses, each canonical map can represent the density of the canonical structure in one spatial region, and each flow generator can generate the deformation for that region. In other uses, each canonical density can represent one discrete object, and the model can have an additional discrete latent variable capturing which object is present in the particle image. Furthermore, regularizers and constraints can be applied straightforwardly to, for example, enforce that the output of the flow generator in a certain region is zero, or that two regions of the protein object have the same structure (symmetry) or that one region moves rigidly but is attached to another region that deforms non-rigidly. In general, any combination of at least one canonical map, flow generator, and any other components can be used to compose the image formation process within the method described herein.

Although the invention has been described with reference to certain specific embodiments, various modifications thereof will be apparent to those skilled in the art without departing from the spirit and scope of the invention as outlined in the claims appended hereto. The entire disclosures of all references recited above are incorporated herein by reference.

The invention claimed is:

1. A computer-implemented method for determining the three-dimensional (3D) structure and 3D motion of a molecule from two-dimensional (2D) or 3D experimental images, the 3D structure in the form of one or more canonical 3D maps represented as a 3D voxel array of real-space density values, and the 3D motion in the form of parameters of one or more machine-learning neural network flow generators, the method comprising:
  receiving the experimental images;
  receiving contrast transfer function (CTF) parameters for each experimental image;
  initializing pose parameters for each experimental image;
  initializing unknown model parameters of generative machine-learning neural network based image formation, the unknown model parameters comprising:
    one or more canonical 3D maps; and
    the parameters of the one or more machine-learning neural network flow generators, each flow generator comprising a parameterized generator function taking as input a latent coordinate vector and outputting a 3D deformation field;
  wherein the generative machine-learning neural network based image formation takes as input at least the latent coordinate vector and outputs a simulated image, the image formation comprising:
    generating one or more 3D deformation fields by inputting the latent coordinate vector into the one or more machine-learning neural network flow generators;
    performing a convection and projection operation by convecting one or more of the canonical 3D maps by the one or more 3D deformation fields, and projecting using the pose parameters for a given experimental image; and
    performing CTF corruption of the projected result using the CTF parameters of the given experimental image to generate the simulated image;
  training the generative machine-learning neural network based image formation by fitting the unknown model parameters to the experimental images by performing one or more iterations of gradient-based optimization of an objective function, the objective function taking as input at least simulated images and experimental images,
  wherein performing at least one of the iterations comprises performing a latent variable search for at least one experimental image, the latent variable search for a given experimental image comprising:
    performing the generative machine-learning neural network based image formation one or more times to generate simulated images from one or more latent coordinate vectors; and
    selecting one or more latent coordinate vectors based on a similarity between the machine-learning generated simulated images and the given experimental image;
  and wherein performing the at least one of the iterations comprises updating at least one of the unknown model parameters using the at least one of the experimental images, the updating the at least one of the unknown model parameters comprising:
    generating simulated images by performing the generative machine-learning neural network based image formation using the one or more selected latent coordinate vectors of each of the at least one of the experimental images;
    evaluating the objective function using at least the machine-learning generated simulated images and the at least one of the experimental images;
    computing the gradient of the objective function with respect to the at least one unknown model parameter to be updated; and
    updating the unknown model parameter using the gradient; and
  outputting the one or more canonical 3D maps and the parameters of the one or more machine-learning neural network flow generators using the trained generative machine-learning neural network based image formation.

2. The method of claim 1, wherein the pose parameters for each experimental image are initialized by receiving them as input.

3. The method of claim 1, wherein the experimental images and the simulated images are 2D.

4. The method of claim 1, wherein the convection and projection operation comprises interpolating the one or more canonical 3D maps to form the convected and projected image, the interpolation operation defined by the one or more 3D deformation fields and the pose parameters for the given experimental image.

5. The method of claim 1, wherein a flow generator of the one or more flow generators is a feed-forward neural network.

6. The method of claim 1, wherein a 3D deformation field is represented as deformed positions of vertices of a mesh of volumetric elements, and wherein deformation vector field values are defined by interpolation within the volume of each mesh element.

7. The method of claim 1, wherein the objective function comprises at least a negative log-likelihood of a simulated image given an experimental image using a noise model.

8. The method of claim 7, wherein the noise model is a Gaussian noise model.

9. The method of claim 1, wherein the latent variable search comprises coordinate descent search over the latent coordinate vector space.

10. The method of claim 1, wherein the latent variable search comprises gradient descent search over the latent coordinate vector space.

11. The method of claim 1, wherein the latent variable search comprises selecting latent coordinate vectors that are equal to the latent coordinate vectors determined to optimize the similarity plus a component of random noise.

12. The method of claim 1, wherein each iteration of the gradient-based optimization comprises selecting a random subset of the experimental images.

13. The method of claim 1, wherein updating at least one of the unknown model parameters using the gradient is performed using the Adam update rule.

14. The method of claim 1, wherein updating at least one of the unknown model parameters using the gradient is performed using the Stochastic Gradient Descent update rule.

15. The method of claim 1, wherein updating at least one of the unknown model parameters using the gradient is performed using the Stochastic Gradient Descent with momentum update rule.

16. The method of claim 1, wherein updating at least one of the unknown model parameters using the gradient is performed using the Limited-memory-Broyden-Fletcher-Goldfarb-Shanno (L-BFGS) update rule.

17. The method of claim 1, wherein the objective function comprises regularizing terms.

18. The method of claim 17, wherein regularizing terms comprise terms that penalize non-rigid deformation in a 3D deformation field.

19. The method of claim 18, wherein a 3D deformation field is represented as deformed positions of vertices of a mesh of volumetric elements, the deformation vector field values defined by interpolation within the volume of each mesh element, and regularizing terms comprise terms that penalize non-rigid deformation within each mesh element.

20. The method of claim 1, wherein the optimization of the unknown model parameters is performed using spatial frequency marching.

21. The method of claim 1, wherein the optimization of the unknown model parameters is first performed using a lower spatial frequency limit and subsequently performed using a higher spatial frequency limit.

* * * * *